US012465781B2

(12) United States Patent
Park

(10) Patent No.: US 12,465,781 B2
(45) Date of Patent: Nov. 11, 2025

(54) NEGATIVE POISSON'S RATIO MATERIALS FOR THERMAL AND RADIATION THERAPY SEEDS

(71) Applicant: Joon Bu Park, Las Vegas, NV (US)

(72) Inventor: Joon Bu Park, Las Vegas, NV (US)

( * ) Notice: Subject to any disclaimer, the term of this patent is extended or adjusted under 35 U.S.C. 154(b) by 1155 days.

(21) Appl. No.: 17/345,486

(22) Filed: Jun. 11, 2021

(65) Prior Publication Data

US 2022/0395705 A1 Dec. 15, 2022

(51) Int. Cl.
*A61N 5/10* (2006.01)
*A61N 1/40* (2006.01)
*B33Y 80/00* (2015.01)

(52) U.S. Cl.
CPC .............. *A61N 1/406* (2013.01); *B33Y 80/00* (2014.12); *A61N 5/1007* (2013.01)

(58) Field of Classification Search
CPC .... A61N 2005/1019; A61N 2005/1024; A61N 2005/1025; A61N 5/1027
See application file for complete search history.

(56) References Cited

U.S. PATENT DOCUMENTS 5,035,713 A * 7/1991 Friis .................... A61F 2/30767 623/23.52
6,780,361 B1 8/2004 Sridharan et al.
7,488,854 B2 2/2009 Seo et al.
8,932,340 B2 1/2015 Meyer et al.
10,071,012 B2 9/2018 Larson et al.
10,314,700 B2 6/2019 Sogard et al.
10,696,034 B2 6/2020 Pattinson et al.
10,842,205 B2 11/2020 Lee et al.
10,994,057 B2 5/2021 Williams et al.
2003/0219866 A1 11/2003 Kruijer
2005/0003011 A1 1/2005 Sridharan et al.
2006/0084167 A1 4/2006 Cohenford et al.
2006/0293656 A1 12/2006 Shadduck et al.

(Continued)

FOREIGN PATENT DOCUMENTS

EP 1645255 4/2006
WO WO 2005/072419 8/2005

(Continued)

OTHER PUBLICATIONS

Ali et al., "An Auxetic Structure Configured as Oesophageal Stent with Potential to be used for Palliative Treatment of Oesophageal Cancer; Development and In Vitro Mechanical Analysis," Journal of Materials Science—Materials in Medicine, Sep. 2011, 22(11):2573-2581.

(Continued)

*Primary Examiner* — Samuel G Gilbert
(74) *Attorney, Agent, or Firm* — Fish & Richardson P.C.

(57) ABSTRACT

A biocompatible seed for implantation in tissue of a patient includes an elongated body sized and shaped to be at least partially inserted into the tissue of the patient, in which the body includes a negative Poisson's ratio (NPR) material having a Poisson's ratio of between 0 and −1. The seed can be a thermal seed configured to generate heat responsive to exposure to a magnetic field. The seed can be a seed for brachytherapy that includes an inner layer including a radioactive material and an outer layer including the NPR material.

20 Claims, 7 Drawing Sheets

(56) References Cited

U.S. PATENT DOCUMENTS

| | | | | |
|---|---|---|---|---|
| 2007/0213838 | A1* | 9/2007 | Hengelmolen | A61F 2/915 606/108 |
| 2011/0059291 | A1* | 3/2011 | Boyce | C08J 5/18 428/218 |
| 2011/0200526 | A1* | 8/2011 | Parsai | A61N 1/406 424/1.29 |
| 2018/0243524 | A1 | 8/2018 | Virr | |
| 2018/0243525 | A1 | 8/2018 | Virr et al. | |
| 2018/0344977 | A1 | 12/2018 | Nierenberger et al. | |
| 2020/0352585 | A1 | 11/2020 | Losordo et al. | |
| 2021/0069482 | A1 | 3/2021 | Ryu et al. | |
| 2021/0113083 | A1 | 4/2021 | Araci et al. | |
| 2021/0113356 | A1 | 4/2021 | Laszczak et al. | |

FOREIGN PATENT DOCUMENTS

| | | |
|---|---|---|
| WO | WO 2008/067304 | 6/2008 |
| WO | WO 2008/097592 | 8/2008 |
| WO | WO 2019/126199 | 6/2019 |
| WO | WO 2019/173784 | 9/2019 |
| WO | WO 2020/017963 | 1/2020 |
| WO | WO 2020/060558 | 3/2020 |
| WO | WO 2020/061379 | 3/2020 |
| WO | WO 2020/146777 | 7/2020 |
| WO | WO 2020/197854 | 10/2020 |
| WO | WO 2021/042044 | 3/2021 |

OTHER PUBLICATIONS

Choi et al., "Non-linear properties of polymer cellular materials with a negative Poisson's ratio," Journal of Materials Science, Sep. 1992, 27: 4678-4684.

Friis et al., "Negative Poisson's ratio polymeric and metallic foams," Journal of Materials Science, Dec. 1988, 23: 4406-4414.

Martz et al., "Re-entrant Transformation Methods in Closed Cell Foams," Cellular Polymers, 1996, 15:229-249.

Paulus et al., "Corrosion analysis of NiCu and PdCo thermal seed alloys used as interstitial hyperthermia implants," Biomaterials, Dec. 1997, 18(24):1609-1614.

Paulus et al., "Evaluation of inductively heated ferromagnetic alloy implants for therapeutic interstitial hyperthermia," IEEE Transactions on Biomedical Engineering, Apr. 1996, 43(4):406-413.

International Preliminary Report on Patentability in International Appln. No. PCT/US2022/032609, mailed on Dec. 21, 2023, 9 pages.

Ali, "Development of Auxetic Polymeric Stent-graft for the palliative Treatment of Oesophageal Cancer," University of Sheffield, Jun. 2012, 305 pages.

Gautam, "Study of dosimetric and thermal properties of a newly developed thermo-brachytherapy seed for treatment of solid tumors," University of Toledo, May 2013, 161 pages.

International Search Report and Written Opinion in International Application No. PCT/US22/32609, dated Nov. 7, 2022, 13 pages.

* cited by examiner

NEGATIVE POISSON'S RATIO MATERIALS FOR THERMAL AND RADIATION THERAPY SEEDS

BACKGROUND

The present disclosure relates generally to materials for seeds for thermal and radiation therapy.

SUMMARY

Thermal therapy and radiation therapy (e.g., brachytherapy) are non-invasive procedures to treat abnormal growths or tumors in the body (e.g., Benign Prostatic Hyperplasia (BPH), Adenocarcinoma of the prostate (CaP)). BPH is a common tumor in men, and is classified by abnormal growth in the transition zone and periurethral tissue surrounding the urethra. As the adenomatous tissue within the transition zone expands, it can compress or block the urethra, causing irritation and obstruction. CaP, another prostate growth, is a commonly diagnosed cancer in the U.S. male population. Treatments for BPH and CaP can include surgery, medications, thermal therapy, or radiation therapy. Thermal therapy and radiation therapy can also be used to treat other types of abnormal growths or tumors.

Thermal therapy at moderate temperatures (e.g., about 41-45° C.) promotes changes in cellular dynamics. Immediate effects of thermal exposure in this temperature range include acceleration of metabolism, thermal inactivation of enzymes, and rupture of cell membranes. Other effects include intracellular and tissue edema as well as an increase in blood vessel permeability and dilatation. For low temperatures and shorter exposure times, the damage due to thermal effects alone can be reversible. For longer times or higher temperatures, cellular repair mechanisms can no longer keep up, or can lose function due to thermal damage of key enzymes, and cell death and tissue necrosis can occur, e.g., within 3-5 days.

The localization of high-temperature hyperthermia at temperatures greater than about 45-50° C. can be used to selectively destroy or permanently alter tissue regions. In the high-temperature range, thermal coagulation and necrosis can occur in tissues exposed to temperatures greater than 50-55° C. for a duration of about 1-2 minutes or shorter times for even higher temperatures. Thermal exposure to these high temperatures can cause cellular and tissue structural proteins to undergo irreversible denaturation and conformational changes. These thermal effects can be lethal and immediate, producing thermally coagulated tissue. On the extreme end, temperatures close to or greater than 100° C. can cause ablation of tissue.

We describe here implants used to deliver thermal therapy or radiation therapy that include materials having a negative Poisson's ratio ("NPR materials"). NPR materials are lightweight and porous, and are capable of being embedded securely in the surrounding tissue due to their porosity and high surface area. Implants, such as thermal seeds or radioactive seeds for brachytherapy, can be formed of NPR materials alone or in conjunction with materials having a positive Poisson's ratio ("PPR materials"). In some examples, some portions of the seeds are formed of NPR materials and other portions are formed of PPR materials. In some examples, composite materials that include both NPR materials and PPR materials are used for the seeds.

In an aspect, a biocompatible seed for implantation in tissue of a patient includes an elongated body sized and shaped to be at least partially inserted into the tissue of the patient, in which the body includes a negative Poisson's ratio (NPR) material having a Poisson's ratio of between 0 and −1.

Embodiments can include one or any combination of two or more of the following features.

The elongated body is a generally cylindrical body having an increasing diameter from a first end to a second end, the first end being configured to be inserted into the tissue of the patient.

The NPR material includes a porous NPR metal material.

The porous NPR metal material includes one or more of nickel, copper, palladium, or cobalt.

The porous NPR metal material includes an NPR metal foam.

The NPR material has a Poisson's ratio of between 0 and −0.8.

The NPR material is composed of a cellular structure having a characteristic dimension of between 0.01 μm and 3 mm.

The body includes a composite material including the NPR material and a positive Poisson's ratio (PPR) material.

The body includes alternating layers of the NPR material and a PPR material.

The alternating layers are oriented parallel to a longitudinal axis of the elongated body.

The body includes an inner layer and an outer layer covering the inner layer, and the outer layer includes the NPR material.

The interior layer includes a PPR material.

The interior layer includes a metal.

The seed includes a seed for brachytherapy, and the inner layer includes a radioactive material.

The seed includes a thermal seed configured to generate heat responsive to exposure to a magnetic field.

In an aspect, a method of making a seed for implantation in tissue of a patient includes forming an elongated body from an NPR material having a Poisson's ratio of between 0 and −1, including forming the body in a size to be partially inserted into the tissue of the patient.

Embodiments can include one or any combination of two or more of the following features.

Forming the body includes heating and compressing a PPR material to form the NPR material.

Forming the body includes forming the body from nano- or micro-structured PPR materials.

Forming the body includes forming the body using an additive manufacturing technique.

Forming the body includes forming an outer layer of the body from the NPR material, in which the outer layer covers an inner layer of the body.

The inner layer of the body includes a radioactive material.

In an aspect, a method of thermally treating tissue includes implanting into the tissue one or more implantable seeds, each seed including: an elongated body sized and shaped to be at least partially inserted into the tissue of the patient, in which the body includes an NPR material having a Poisson's ratio of between 0 and −1; and applying a magnetic field to the implanted seeds, in which application of the magnetic field induces an electrical current in each seed, the electrical current generating heat for thermal treatment of the tissue.

In an aspect, a method of treating a tumor with a brachytherapy treatment includes implanting into the tumor one or more implantable seeds, each seed including an elongated body sized and shaped to be at least partially inserted into the tumor, in which the body includes: an inner layer formed of a radioactive material, and an outer layer covering the inner layer, the outer layer including an NPR material having a Poisson's ratio of between 0 and −1; and allowing the implantable seeds to remain in the tumor for a predetermined amount of time to deliver radiation to the tumor.

Other implementations are within the scope of the claims.

DETAILED DESCRIPTION

We describe here implants used in thermal therapy (e.g., thermal seeds) or radiation therapy (e.g., brachytherapy seeds) that include materials having a negative Poisson's ratio ("NPR materials"). NPR materials are lightweight, porous, and capable of being embedded in the surrounding tissue more securely than conventional implants due to their porosity and greater surface area in contact with tissue. Implants can be formed of NPR materials alone or in conjunction with materials having a positive Poisson's ratio ("PPR materials"). In some examples, some portions of the seeds are formed of NPR materials and other portions are formed of PPR materials. In some examples, composite materials that include both NPR materials and PPR materials are used for the seeds.

Figure 1:
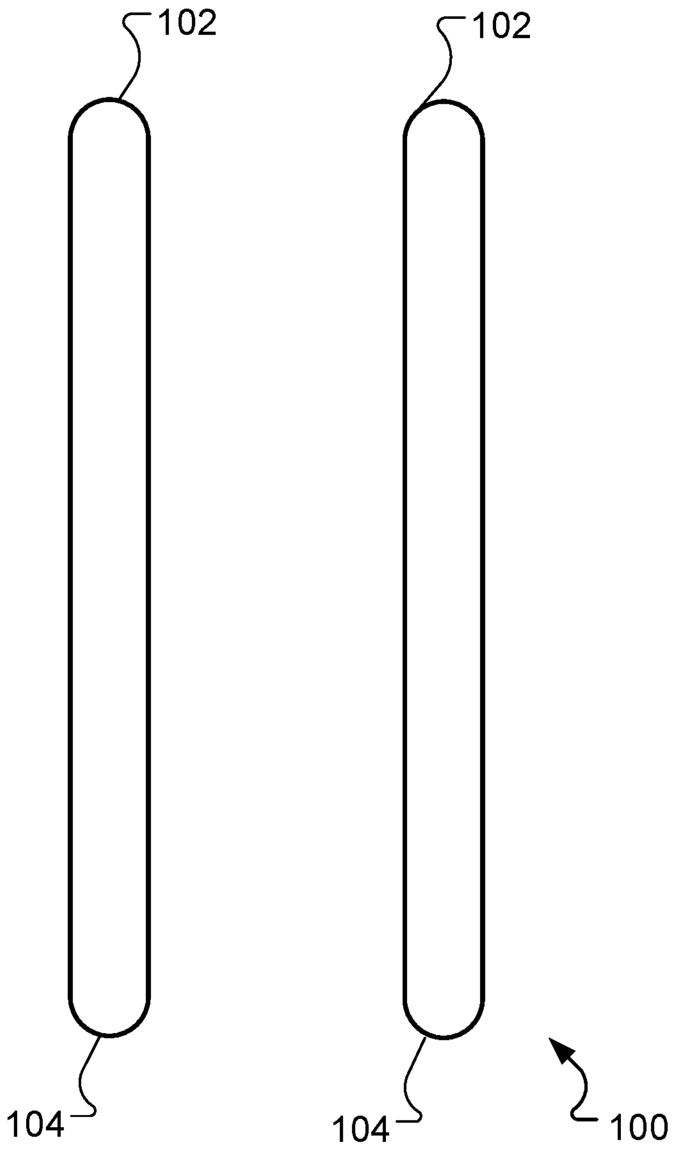
FIG. 1 is an illustration of thermal seeds.

Referring to FIG. 1, a set of thermal seeds 100 is illustrated. The thermal seeds 100 have an elongated body that is sized and shaped to be at least partially inserted into a patient (e.g., a prostate of a patient). For instance, the elongated body of the thermal seeds 100 can be generally cylindrical, e.g., with a diameter of about 1 millimeters (mm) and a length of about 10 mm. Although the thermal seeds are illustrated in a generally cylindrical shape, the thermal seeds can be a variety of shapes that fill the prostate (e.g., hexagonal, octagonal, elliptical, etc.). Additionally, the thermal seeds can have a variable diameter from a proximal end 102 to a distal end 104.

In some examples, thermal seeds are formed of a biocompatible metal or metal alloy, such as Nickel (Ni), Copper (Cu), Palladium (Pd), Cobalt (Co), NiCu, PdCo, or other suitable materials. To use such thermal seeds in, e.g., treatment of BPH, the thermal seeds are inserted into the prostate of the patient. Once in the prostate, the thermal seeds can be heated through, e.g., magnetic induction. Magnetic induction is the creation of electromagnetic forces (e.g., inducing an electrical current) using an electrical conductor (e.g., the thermal seeds 100) and changing magnetic fields. The induced electrical current in the thermal seeds can create heat for application of thermal therapy to the tissue in which the seeds are implanted, e.g., to the prostate.

The thermal seeds 100 described here can be at least partially formed of a biocompatible NPR material (also referred to as an auxetic material). In some examples, the thermal seeds 100 are formed completely of a biocompatible NPR material, such as a porous NPR material, e.g., a porous NPR metal material. In some examples, the porous material is an NPR foam material, e.g., an NPR metal foam. In some examples, the thermal seeds 100 are formed of a composite material that include both biocompatible NPR materials and biocompatible PPR materials, referred to as an NPR-PPR composite material. Forming the thermal seeds 100 from an NPR material can have advantages. For instance, NPR materials, such as porous NPR materials, e.g., NPR foam materials, have a low density, and seeds formed from NPR materials can be less obtrusive to a patient than comparable PPR seeds. In addition, porous NPR materials, such as NPR foam materials, thus present a large surface area to the tissue in which the NPR seed is implanted, facilitating good contact between the seed and the tissue. This good contact can help with positional stability of the seed. The large area of contact between the seed and the tissue also helps ensure efficient heat transfer from the seed to the tissue, contributing to therapeutic effectiveness.

An NPR material is a material that has a Poisson's ratio that is less than zero, such that when the material experiences a positive strain along one axis (e.g., when the material is stretched), the strain in the material along the two perpendicular axes is also positive (e.g., the material expands in cross-section). Conversely, when the material experiences a negative strain along one axis (e.g., when the material is compressed), the strain in the material along a perpendicular axis is also negative (e.g., the material compresses along the perpendicular axis). By contrast, a PPR material has a Poisson's ratio that is greater than zero. When a PPR material experiences a positive strain along one axis (e.g., when the material is stretched), the strain in the material along the two perpendicular axes is negative (e.g., the material compresses in cross-section), and vice versa.

Figure 2:
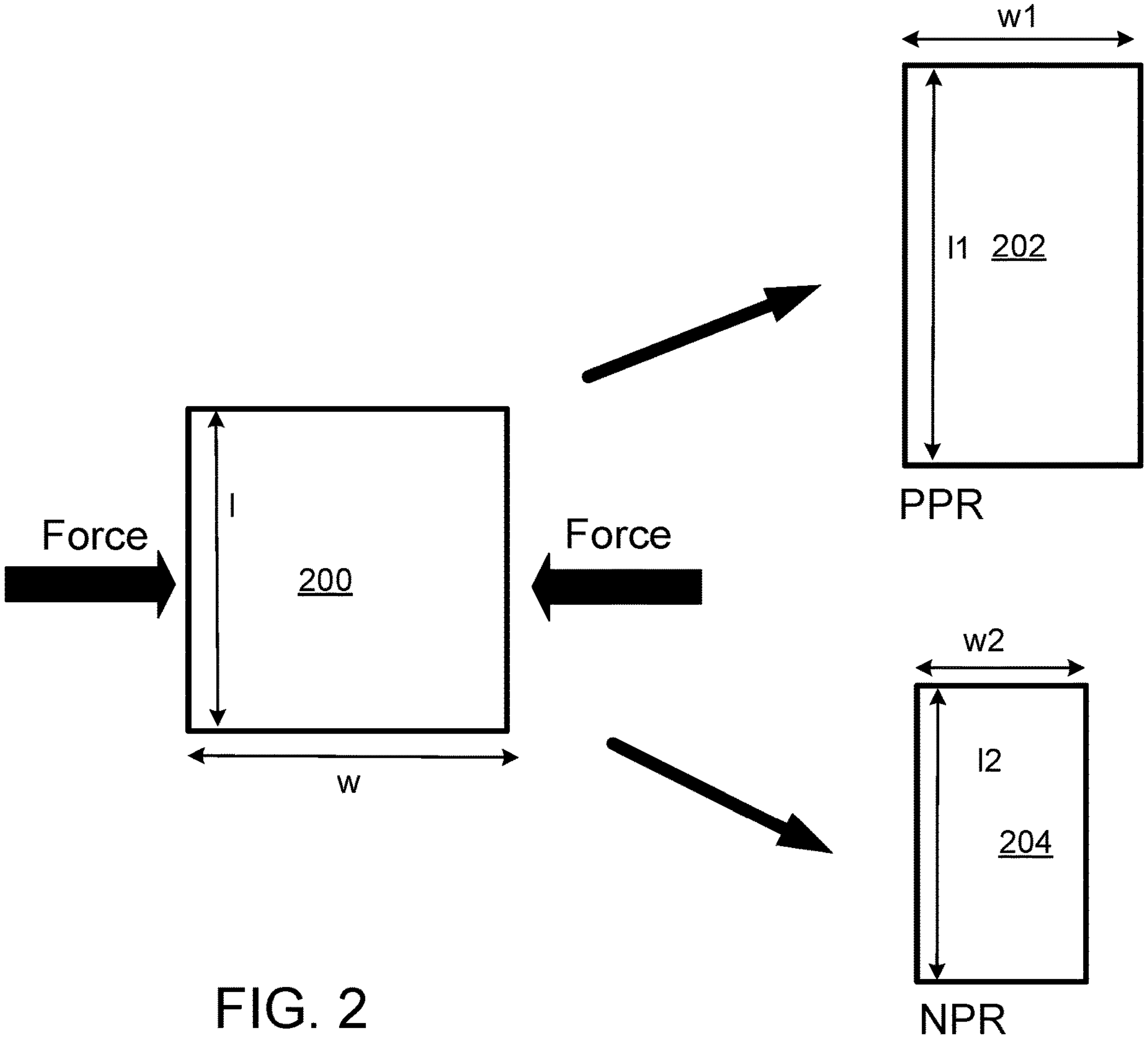
FIG. 2 is an illustration of materials with negative and positive Poisson's ratios.

Materials with negative and positive Poisson's ratios are illustrated in FIG. 2, which depicts a hypothetical two-dimensional block of material 200 with length l and width w.

If the hypothetical block of material 200 is a PPR material, when the block of material 200 is compressed along its width w, the material deforms into the shape shown as block 202. The width w1 of block 202 is less than the width w of block 200, and the length l1 of block 202 is greater than the length l of block 200: the material compresses along its width and expands along its length.

By contrast, if the hypothetical block of material 200 is an NPR material, when the block of material 200 is compressed along its width w, the material deforms into the shape shown as block 204. Both the width w2 and the length l2 of block 204 are less than the width w and length l, respectively, of block 200: the material compresses along both its width and its length.

NPR materials for thermal seeds can be foams, such as polymeric foams, ceramic foams, metallic foams, or combinations thereof. A foam is a multi-phase composite material in which one phase is gaseous and the one or more other phases are solid (e.g., polymeric, ceramic, or metallic). Foams can be closed-cell foams, in which each gaseous cell is sealed by solid material; open-cell foams, in which the each cell communicates with the outside atmosphere; or mixed, in which some cells are closed and some cells are open.

An example of an NPR foam structure is a re-entrant structure, which is a foam in which the walls of the cells are concave, e.g., protruding inwards toward the interior of the cells. In a re-entrant foam, compression applied to opposing walls of a cell will cause the four other, inwardly directed walls of the cell to buckle inward further, causing the material in cross-section to compress, such that a compression occurs in all directions. Similarly, tension applied to opposing walls of a cell will cause the four other, inwardly directed walls of the cell to unfold, causing the material in cross-section to expand, such that expansion occurs in all directions. NPR foams can have a Poisson's ratio of between −1 and 0, e.g., between −0.8 and 0, e.g., −0.8, −0.7, −0.6, −0.5, −0.4, −0.3, −0.2, or −0.1. NPR foams can have an isotropic Poisson's ratio (e.g., Poisson's ratio is the same in all directions) or an anisotropic Poisson's ratio (e.g., Poisson's ratio when the foam is strained in one direction differs from Poisson's ratio when the foam is strained in a different direction).

An NPR foam can be polydisperse (e.g., the cells of the foam are not all of the same size) and disordered (e.g., the cells of the foam are randomly arranged, as opposed to being arranged in a regular lattice). An NPR foam can have a characteristic dimension (e.g., the size of a representative cell, such as the width of the cell from one wall to the opposing wall) ranging from 0.01 μm to about 3 mm, e.g., about 0.01 μm, about 0.05 μm, about 0.1 μm, about 0.5 μm, about 1 μm, about 10 μm, about 50 μm, about 100 μm, about 900 μm, about 1 mm, about 2 mm, or about 3 mm.

Examples of polymeric foams for thermal seeds include thermoplastic polymer foams (e.g., polyester polyurethane or polyether polyurethane); viscoelastic elastomer foams; or thermosetting polymer foams such as silicone rubber. Examples of metallic foams include metallic foams based on Nickel (Ni), Copper (Cu), Palladium (Pd), Cobalt (Co), NiCu, PdCo, or other metals or alloys.

NPR-PPR composite materials are composites that include both regions of NPR material and regions of PPR material. NPR-PPR composite materials can be laminar composites, matrix composites (e.g., metal matrix composites, polymer matrix composites, or ceramic matrix composites), particulate reinforced composites, fiber reinforced composites, or other types of composite materials. In some examples, the NPR material is the matrix phase of the composite and the PPR material is the reinforcement phase, e.g., the particulate phase or fiber phase. In some examples, the PPR material is the matrix phase of the composite and the NPR material is the reinforcement phase.

Figure 3:
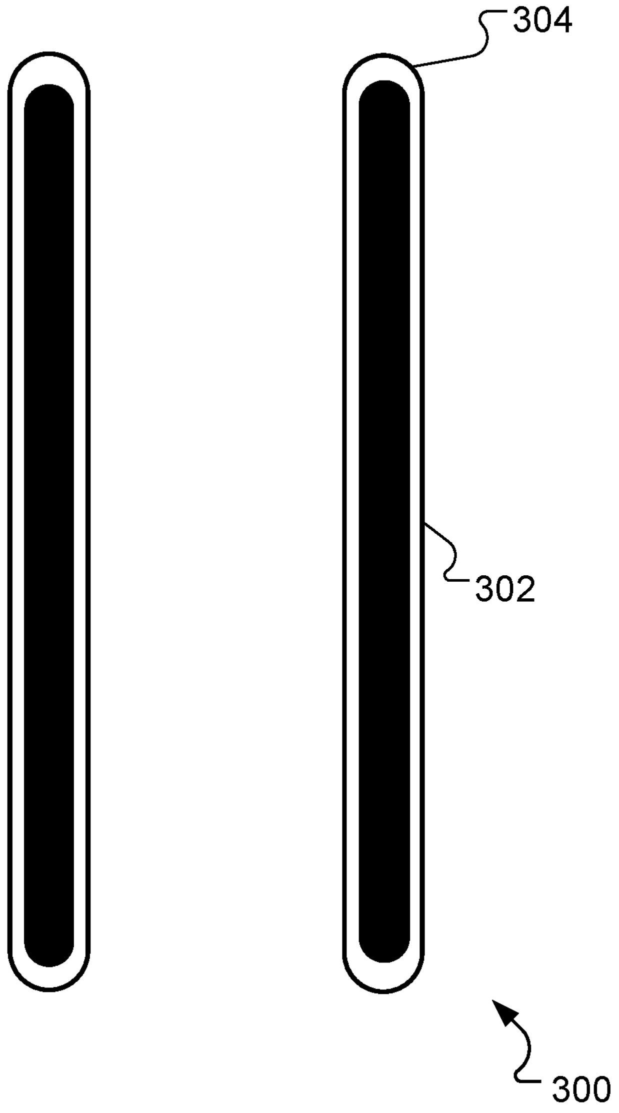
FIG. 3 is an illustration of thermal seeds.

In some examples, thermal seeds can be multilayer structures. With reference to FIG. 3, thermal seeds 300 have an inner layer 302 and an outer layer 304. The inner layer 302 can have a diameter of, e.g., about 0.01 millimeters to about 14.9 millimeters, and the outer layer 304 can have a thickness of, e.g., about 0.01 millimeters to about 14.9 millimeters.

The inner layer 302 and the outer layer 304 are formed of different materials. The different composition of the inner layer 302 and outer layer 304 can allow for desired performance characteristics to be achieved. For instance, the inner layer 302 can be formed of a material with a high thermal capacity or thermal conductivity to facilitate effective thermal therapy, and the outer layer 304 can be formed of a biocompatible NPR material to provide a porous exterior that gives a large surface area in contact with the surrounding tissue. In some examples, the outer layer 304 is a non-porous material that acts as a barrier layer to prevent contact between the inner layer 302 and the surrounding tissue. In some examples, the outer layer 304 makes the thermal seeds comfortable for the patient, e.g., the outer layer is formed of a low friction material (e.g., the outer layer has a lower coefficient of friction than the inner layer with respect to the patient's prostate), a softer material that conforms better to a patient's prostate than the material of the inner layer, or a moldable material. In an example, the outer layer 302 is formed of an NPR material, such as a porous NPR material, e.g., an NPR polymer foam or an NPR metal foam, or an NPR-PPR composite material; and the inner layer is formed of a PPR material, such as a metal or metal alloy, e.g., Nickel (Ni), Copper (Cu), Palladium (Pd), Cobalt (Co), NiCu, PdCo, or another suitable material; or vice versa. An outer layer composed of an NPR material can be advantageous because the seeds can be embedded in the surrounding tissue, e.g., prostate, more securely due to the porosity and increased surface area in contact with the tissue.

In some examples, thermal seeds have more than two layers (e.g., 3 layers, 4 layers, etc.). In implementations with more than two layers, each layer can be formed of a different material, or multiple layers can be formed of the same material.

Figure 4:
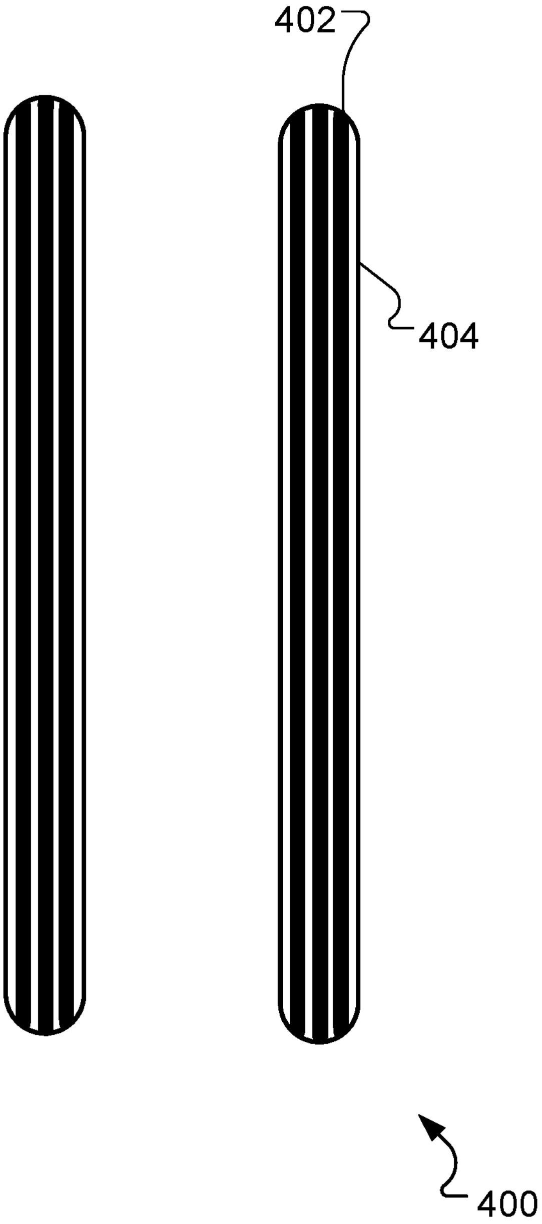
FIG. 4 is an illustration of thermal seeds.

In some embodiments, thermal seeds can be composed of multiple layers of PPR and NPR materials. For example, with reference to FIG. 4, thermal seeds 400 have PPR layers 402 and NPR layers 404 that extend longitudinally along the thermal seeds 400, e.g., along an axis aligned with the elongated length of the thermal seeds 400. In the illustrated example, the thermal seeds 400 have three PPR layers 402 and four NPR layers 404, however in other embodiments the thermal seeds can have more or fewer layers. The PPR layers 402 and the NPR layers 404 are of even width, although in other embodiments the widths of the layers can be irregular. In some embodiments, the multiple layers of PPR and NPR materials can be arranged laterally rather than longitudinally, e.g., perpendicular to the longitudinal axis of the thermal seeds. In other embodiments, the multiple layers of PPR and NPR materials can be arranged obliquely to the thermal seeds, e.g., neither parallel to nor perpendicular to the longitudinal axis of the thermal seeds.

Figure 5:
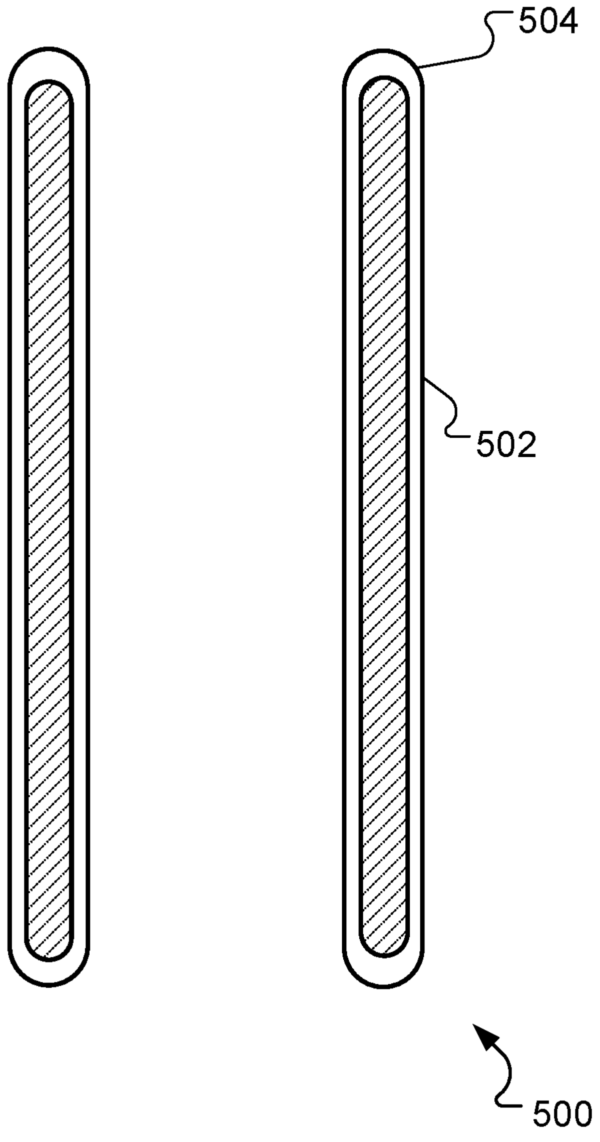
FIG. 5 is an illustration of radioactive seeds.

Other types of therapy, such as radiation therapy (e.g., brachytherapy) can utilize seeds formed of an NPR material. With reference to FIG. 5, seeds 500 include an outer layer 504 formed of an NPR material or an NPR-PPR composite material and an inner layer 502 formed of a radioactive material (e.g., radium, cesium, iridium, iodine, phosphorus, palladium). The inner layer 502 is partially or completely encapsulated within the outer layer 502. The outer layer 504 can be an NPR foam material, such as a porous NPR material, e.g., an NPR polymer foam, an NPR ceramic foam, or an NPR metal foam. An outer layer composed of an NPR material, such as a porous NPR material, e.g., an NPR foam material, can be advantageous because the seeds can be embedded in the surrounding tissue, e.g., prostate, more securely due to the porosity and increased surface area in contact with the tissue. Some porous NPR materials, e.g., NPR foam materials, are relatively soft, moldable, or both, allowing the seeds to conform well to the surrounding tissue, which helps ensure positional stability. In some examples, the porous NPR material, e.g., NPR foam material, of the outer layer 504 can be low friction material (e.g., the outer layer has a lower coefficient of friction than the inner layer with respect to the patient's prostate), which can help make the insertion of the seeds 500 less irritating to the patient's tissue. In some embodiments, the NPR and PPR layers can be arranged similarly to the arrangement of multiple NPR and PPR layers of FIG. 4.

Using radioactive seeds in a brachytherapy procedure can allow a higher dose of radiation to be delivered to a limited area than conventional, external beam radiation treatments. Radioactive seeds can be more effective at destroying cancer cells than conventional radiation treatments while minimizing damage to surrounding normal tissue. The radiation emitted from the inner layer 502 can kill damaging tumors or cells (e.g., cancer cells). The outer layer 504 is formed of a material that does not interfere with the radiation emitted from the inner layer 502.

Figure 6:
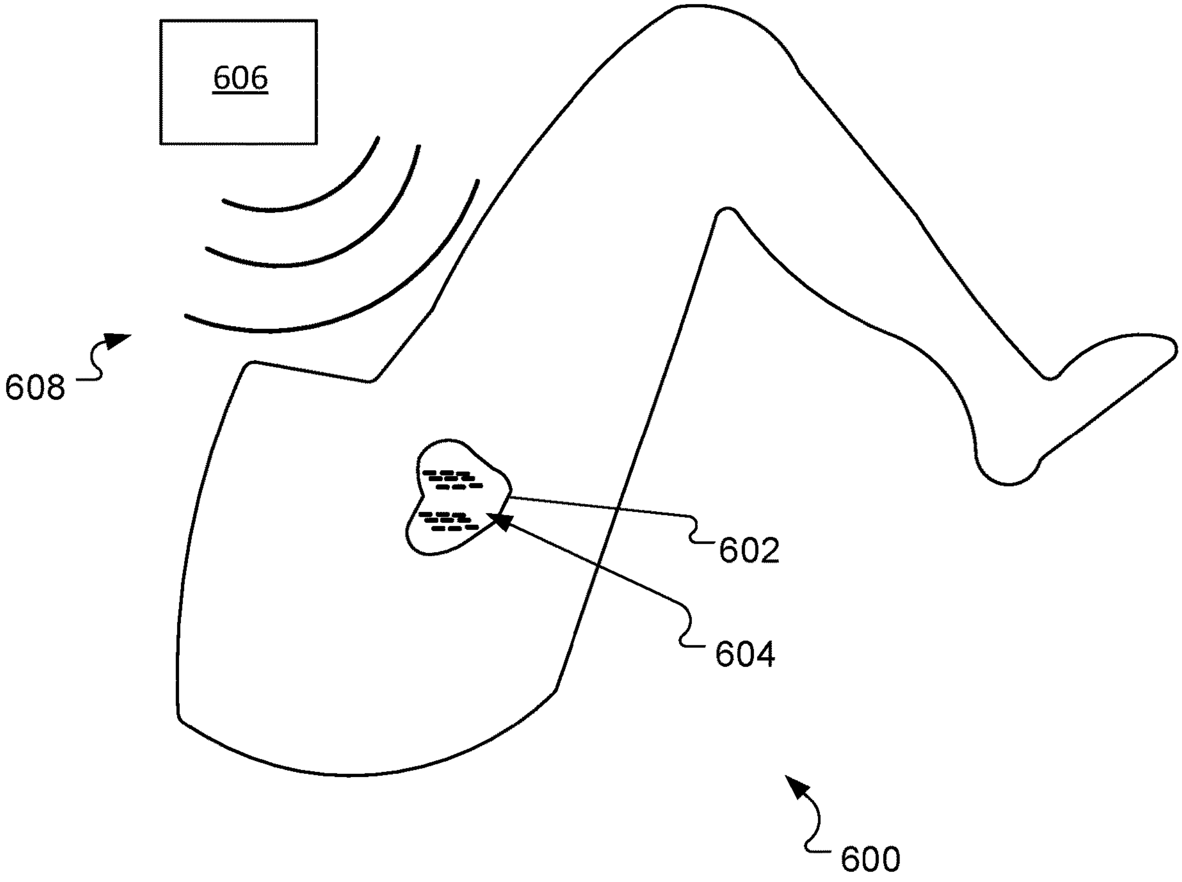
FIG. 6 is an illustration of seeds implanted in a patient.

FIG. 6 illustrates thermal seeds 604 implanted in a patient 600. For example, the seeds 604 are implanted in a prostate 602 of the patient 600. A magnetic field source 606 applies a magnetic field 608 to the seeds, inducing electromagnetic forces in the seeds 604 through magnetic induction. As described above, magnetic induction is the creation of electromagnetic forces (e.g., inducing an electrical current) using an electrical conductor (i.e., thermal seeds) and changing magnetic fields. The induced electrical current in the seeds creates heat for thermal therapy of the surrounding tissue, e.g., the prostate 602.

In the case of brachytherapy, the implanted seeds are radioactive and emit radiation, and the magnetic field source 606 is not necessary. The seeds are implanted in the tissue, e.g., in a tumor, and allowed to remain in the tumor for a predetermined amount of time sufficient to deliver a clinically meaningful amount of radiation to the tumor.

In some examples, porous NPR materials, such as NPR foams, are produced by transformation of PPR foams to change the structure of the foam into a structure that exhibits a negative Poisson's ratio. In some examples, porous NPR materials, such as NPR foams, are produced by transformation of nanostructured or microstructured PPR materials, such as nanospheres, microspheres, nanotubes, microtubes, or other nano- or micro-structured materials, into a foam structure that exhibits a negative Poisson's ratio. The transformation of a PPR foam or a nanostructured or microstructured material into an NPR foam can involve thermal treatment (e.g., heating, cooling, or both), application of pressure, or a combination thereof. In some examples, PPR materials, such as PPR foams or nanostructured or microstructured PPR materials, are transformed into NPR materials by chemical processes, e.g., by using glue. In some examples, NPR materials are fabricated using micromachining or lithographic techniques, e.g., by laser micromachining or lithographic patterning of thin layers of material. In some examples, NPR materials are fabricated by additive manufacturing (e.g., three-dimensional (3D) printing) techniques, such as stereolithography, selective laser sintering, or other appropriate additive manufacturing technique.

In an example, a PPR thermoplastic foam, such as an elastomeric silicone film, can be transformed into an NPR foam by compressing the PPR foam, heating the compressed foam to a temperature above its softening point, and cooling the compressed foam. In an example, a PPR foam composed of a ductile metal can be transformed into an NPR foam by uniaxially compressing the PPR foam until the foam yields, followed by uniaxially compression in other directions.

Figure 7:
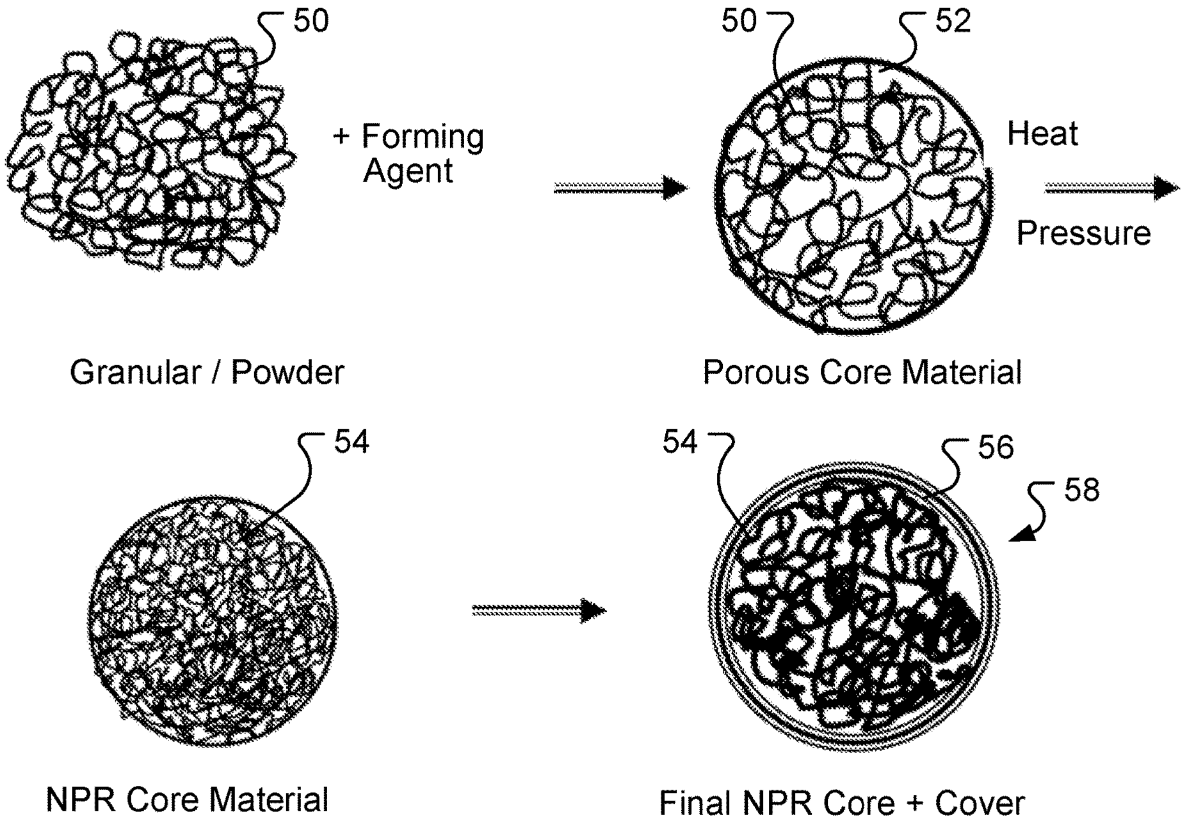
FIG. 7 is a diagram of a method of making an NPR material.

FIG. 7 illustrates an example method of making a multilayer thermal seed in which an inner layer is formed of an NPR material. A granular or powdered material, such as a polymer material (e.g., a rubber) is mixed with a foaming agent to form a porous material 50. The porous material 50 is placed into a mold 52. Pressure is applied to compress the material 50 and the compressed material is heated to a temperature above its softening point. The material is then allowed to cool, resulting in a porous NPR material 54. The porous NPR material 54 is covered with an outer layer 56, such as a polymer layer, and heat and pressure can be applied again to cure the final material into a thermal seed 58.

In some examples, such as for brachytherapy seeds, the outer layer of the seed is formed of an NPR material. A granular or powdered material, such as a polymer material (e.g., a rubber) is mixed with a foaming agent to form a porous material. The porous material is placed into a mold surrounding an inner layer (e.g., a radioactive layer). Pressure is applied to compress the material and the compressed material is heated to a temperature above its softening point. The material is then allowed to cool, resulting in a porous NPR outer layer.

Other methods can also be used to fabricate thermal seeds or brachytherapy seeds formed of an NPR material or an NPR-PPR composite material. For example, various additive manufacturing (e.g., 3D printing) techniques, such as stereolithography, selective laser sintering, or other appropriate additive manufacturing technique, can be implemented to fabricate an thermal seed formed of an NPR material or an NPR-PPR composite. In some examples, different components of the thermal seed are made by different techniques. For example, the inner layer may be 3D printed while the outer layer is not, or vice versa. Additive manufacturing techniques can enable seams to be eliminated.

Particular embodiments of the subject matter have been described. Other embodiments are within the scope of the following claims.

What is claimed is:

1. A biocompatible seed for implantation in tissue of a patient, the seed comprising:

an elongated body sized and shaped to be at least partially inserted into the tissue of the patient, in which the body comprises:

an outer layer comprising a negative Poisson's ratio (NPR) material having a Poisson's ratio of between 0 and −1, and an inner layer comprising a positive Poisson's ratio (PPR) material, wherein the outer layer completely surrounds and encloses the inner layer.

2. The biocompatible seed of claim 1, in which the elongated body is a generally cylindrical body having an increasing diameter from a first end to a second end, the first end being configured to be inserted into the tissue of the patient.

3. The biocompatible seed of claim 1, in which the NPR material comprises a porous NPR metal material.

4. The biocompatible seed of claim 3, in which the porous NPR metal material comprises one or more of nickel, copper, palladium, or cobalt.

5. The biocompatible seed of claim 3, in which the porous NPR metal material comprises an NPR metal foam.

6. The biocompatible seed of claim 1, in which NPR material has a Poisson's ratio of between 0 and −0.8.

7. The biocompatible seed of claim 1, in which the NPR material is composed of a cellular structure having a characteristic dimension of between 0.01 μm and 3 mm.

8. The biocompatible seed of claim 1, in which the body comprises a composite material comprising the NPR material and a positive Poisson's ratio (PPR) material.

9. The biocompatible seed of claim 1, in which the body comprises alternating layers of the NPR material and a PPR material.

10. The biocompatible seed of claim 1, in which the alternating layers are oriented parallel to a longitudinal axis of the elongated body.

11. The biocompatible seed of claim 1, in which the interior layer comprises a metal.

12. The biocompatible seed of claim 1, in which the seed comprises a seed for brachytherapy, and in which the inner layer comprises a radioactive material.

13. The biocompatible seed of claim 1, in which the seed comprises a thermal seed configured to generate heat responsive to exposure to a magnetic field.

14. A method of making a seed for implantation in tissue of a patient, the method comprising:

forming an elongated body from an NPR material having a Poisson's ratio of between 0 and −1, including forming the body in a size to be partially inserted into the tissue of the patient, including:

forming an outer layer from the NPR material, and forming an inner layer from a positive Poisson's ratio (PPR) material, wherein the outer layer completely surrounds and encloses the inner layer.

15. The method of claim 14, in which forming the body comprises heating and compressing a PPR material to form the NPR material.

16. The method of claim 14, in which forming the body comprises forming the body from nano- or micro-structured PPR materials.

17. The method of claim 14, in which forming the body comprises forming the body using an additive manufacturing technique.

18. The method of claim 17, in which forming the body comprises forming an outer layer of the body from the NPR material, in which the outer layer covers an inner layer of the body.

19. The method of claim 18, in which the inner layer of the body comprises a radioactive material.

20. A method of thermally treating tissue, the method comprising:

implanting into the tissue one or more implantable seeds, each seed comprising:

an elongated body sized and shaped to be at least partially inserted into the tissue of the patient, in which the body comprises;

an outer layer comprising an NPR material having a Poisson's ratio of between 0 and −1, and an inner layer comprising a positive Poisson's ratio (PPR) material, wherein the outer layer completely surrounds and encloses the inner layer, applying a magnetic field to the implanted seeds, in which application of the magnetic field induces an electrical current in each seed, the electrical current generating heat for thermal treatment of the tissue.

* * * * *